United States Patent [19]

Nakayama

[11] Patent Number: 5,310,738
[45] Date of Patent: May 10, 1994

[54] PROCESS FOR PRODUCING A HEXAHYDROPYRIDAZINE-1,2-DICARBOXY DERIVATIVE

[75] Inventor: Tadashi Nakayama, Shizuoka, Japan

[73] Assignee: Ihara Chemical Industry Co., Ltd., Tokyo, Japan

[21] Appl. No.: 920,465

[22] PCT Filed: Dec. 26, 1991

[86] PCT No.: PCT/JP91/01772
§ 371 Date: Aug. 17, 1992
§ 102(e) Date: Aug. 17, 1992

[87] PCT Pub. No.: WO92/12136
PCT Pub. Date: Jul. 23, 1992

[30] Foreign Application Priority Data

Dec. 27, 1990 [JP] Japan .................... 2-416789

[51] Int. Cl.$^5$ .......................................... C07D 237/04
[52] U.S. Cl. ................................ 544/224; 564/149; 564/151
[58] Field of Search ............ 544/224; 548/951, 356.1; 564/148, 149, 151; 560/157, 160; 540/553

[56] References Cited

U.S. PATENT DOCUMENTS

| 2,841,584 | 7/1958 | Hunter | 544/224 |
| 4,593,094 | 6/1986 | Nagano et al. | 544/224 |
| 4,906,281 | 3/1990 | Chang | 544/224 |

FOREIGN PATENT DOCUMENTS

53-40785 4/1978 Japan .

OTHER PUBLICATIONS

Zinner et al, *Chemical Abstracts*, vol. 58, No. 4577 (1963).
Dervon et al, *J. Am. Chem. Soc.*, vol. 102, pp. 3863-3870 (1980).

*Primary Examiner*—Emily Bernhardt
*Attorney, Agent, or Firm*—Oblon, Spivak, McClelland, Maier & Neustadt

[57] ABSTRACT

An industrial process which is a process for producing a hexahydropyridazine-1,2-dicarboxy derivative in good yield, is provided. By reacting a hydrazine dicarboxy derivative of the general formula (1):

$$ROC-NH-HN-COR \quad (1)$$

(wherein R is an alkoxy group or an aryl group) with a dihalogenobutane of the general formula (2):

$$X-CH_2CH_2CH_2CH_2-X \quad (2)$$

(wherein X is a chlorine or bromine atom) in the presence of a base selected from an alkali metal carbonate or hydroxide, a hexahydropyridazine-1,2-dicarboxy derivative represented by the general formula:

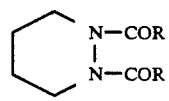

(3)

(wherein R has the same meaning as R in the above general formula (1)) is obtained efficiently.

2 Claims, No Drawings

PROCESS FOR PRODUCING A HEXAHYDROPYRIDAZINE-1,2-DICARBOXY DERIVATIVE

TECHNICAL FIELD

The present invention relates to a process for producing a hexahydropyridazine-1,2-dicarboxy derivative useful as an intermediate material for benzothiazine-type agricultural chemicals such as herbicides.

BACKGROUND ART

Heretofore, with respect to a hexahydropyridazine-1,2-dicarboxy derivative:

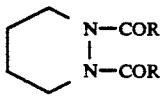
(3)

a process has been proposed, for example, as disclosed in Arch. pharm. 295,526-32(1960), wherein diethylhydrazine dicarboxylate and dibromobutane are reacted in the presence of metal potassium using dimethylformamide as a solvent to obtain diethylhexahydropyridazine-1,2-dicarboxylate.

However, the above conventional process has a problem that metal potassium which is difficult to handle, is required to be used, and besides, the yield in the cyclization is as low as 16%.

The present invention has been accomplished for the purpose of solving the above-mentioned problem of the prior art and providing a process which is an industrial process and which is capable of producing a hexahydropyridazine-1,2-dicarboxy derivative in good yield.

DISCLOSURE OF THE INVENTION

To accomplish the above object, the present invention provides a process for producing a hexahydropyridazine-1,2-dicarboxy derivative represented by the general formula:

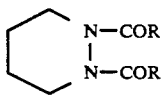
(3)

(wherein R has the same meaning as R in the following general formula (1)), which comprises reacting a hydrazine dicarboxy derivative represented by the general formula:

ROC—NH—HN—COR    (1)

(wherein R is an alkoxy group or an aryl group) with a dihalogenobutane represented by the general formula:

X—CH$_2$CH$_2$CH$_2$CH$_2$—X    (2)

(wherein X is a chlorine or bromine atom) in the presence of a base selected from an alkali metal carbonate or hydroxide.

Namely, the inventors of the present invention have found that the above mentioned hexahydropyridazine-1,2-dicarboxy derivative can be obtained in good yield by using a base selected from an alkali metal carbonate or hydroxide in the production of the hexahydropyridazine-1,2-dicarboxy derivative represented by the general formula (3) by reacting the hydrazine dicarboxy derivative represented by the general formula (1) with the dihalogenobutane represented by the general formula (2), and thus have accomplished the present invention.

Now, the present invention will be described in detail.

In this specification, for example, "the hydrazine dicarboxy derivative represented by the general formula (1)" will be represented by "the hydrazine dicarboxy derivative (1)".

The hydrazine dicarboxy derivative (1) to be used in the present invention, may be the one wherein substituent R in the formula is an alkoxy group or an aryl group. For example, dimethylhydrazine dicarboxylate, dipropyl hydrazine dicarboxylate, diethyl hydrazine dicarboxylate or dibenzoyl hydrazine may be used.

Further, the dihalogenobutane (2) may be the one wherein substituent X in the formula is a chlorine or bromine atom. For example, 1,4-dibromobutane, 1,4-dichlorobutane or 1-bromo-4-chloro-butane may be used.

Further, as the alkali metal carbonate or hydroxide, potassium carbonate, sodium carbonate, sodium hydroxide or potassium hydroxide may, for example, be used. Further, in the above reaction of the hydrazine dicarboxy derivative (1) with the dihalogenobutane (2), a solvent or water may be used to facilitate the stirring. As such a solvent, acetonitrile, benzene, toluene, xylene or dimethylformamide may, for example, be mentioned. In some cases, a phase transfer catalyst such as quaternary ammonium or quaternary phosphonium may be employed.

The ratio of the amounts of the hydrazine carboxy derivative (1), the dihalogenobutane (2) and the alkali metal carbonate or hydroxide may, for example, be within the range of 1:2–10:2–10, preferably, 1:2–5:2–5. The reaction temperature at that time may, for example, be from 10° to 150° C., preferably from 30° C. to the reflux temperature. The reaction time may, for example, be from 2 to 48 hours, preferably form 5 to 24 hours.

Further, the hydrazine dicarboxy derivative (1) to be used as the starting material in h process of the present invention, can readily be prepared by the method disclosed in Organic Synthesis, col. vol. III, p. 375.

On the other hand, the hexahydropyridazine-1,2-dicarboxy derivative (3) obtained by the process of the present invention may, for example, be readily converted to hexahydropyridazine represented by the general formula (4) by the following method:

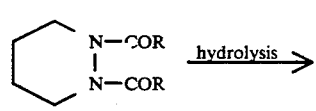

(3)

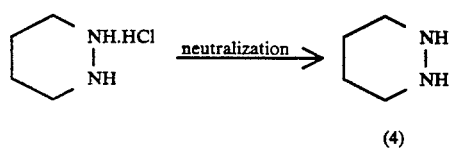

(4)

Further, the hexahydropyridazine (4) thus obtained may, for example, the readily converted to an active compound (5) of a benzothiazine-type herbicide disclosed in Japanese Unexamined Patent Publication No. 264489/1988 by the following method:

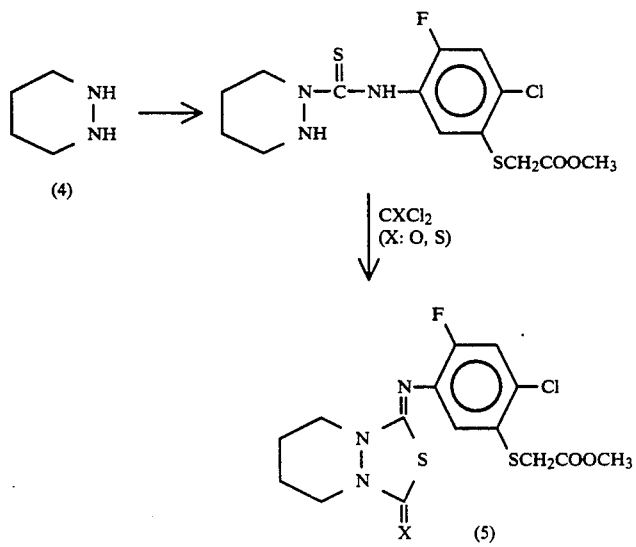

The present invention produces the hexahydropyridazine-1,2-dicarboxy derivative (3) in good yield by reacting the hydrazine dicarboxy derivative (1) with the dihalogenobutane (2) in the presence of a base selected from the alkali metal carbonate or hydroxide, and the hexahydropyridazine-1,2-dicarboxy derivative (3) thus obtained can easily be led to the hexahydropyridazine (4) by the hydrolysis by a mineral acid, followed by a neutralization step, as described above, and the hexahydropyridazine (4) can readily be converted to the active compound (5) of the benzothiazine-type herbicide disclosed in Japanese Unexamined Patent Publication No. 264489/1988. Thus, the present invention is capable of producing an intermediate useful for the active compound of the benzothiazine-type herbicide disclosed in Japanese Unexamined Patent Publication No. 264489/1988 by an industrial process and in good yield.

BEST MODE FOR CARRYING OUT THE INVENTION

Now, the present invention will be described in detail with reference to Examples and Reference Example.

EXAMPLE 1

Preparation of Diethylhexahydropyridazine-1,2-dicarboxylate

Into a 100 ml four necked flask equipped with a reflux condenser, a stirrer and a thermometer, 8.8 g (0.05 mol) of diethylhydrazine dicarboxylate, 13.8 g (0.1 mol) of potassium carbonate and 50 ml of acetonitrile were charged, and 13.0 g (0.06 mol) of dibromobutane was dropwise added under stirring, followed by refluxing under heating for 15 hours. The reaction solution was filtered, concentrated and distilled under reduced pressure to obtain 10.5 g of diethylhexahydropyridazine-1,2-dicarboxylate having a boiling point of 106°–144° C./3 mmHg. The yield was 91%.

EXAMPLES 2 AND 3

The reaction was conducted in the same manner as in Example 1 except that the dihalogenobutane, the base and the solvent were changed. The results are shown in the following Table. In Table 1, TBAB represents tetrabutylammonium bromide.

TABLE 1

| Example No. | Base | Dihalogeno-butane | Solvent | Catalyst | Yield (%) |
|---|---|---|---|---|---|
| 2 | K₂CO₃ | dibromobutane | dimethylformamide | none | 80.9 |
| 3 | K₂CO₃ | dibromobutane | toluene-water | TBAB | 68.3 |

EXAMPLE 4

The reaction was conducted in the same manner as in Example 1 except that diethylhydrazine dicarboxylate was changed to dimethylhydrazine dicarboxylate (but, the same molar amount was used), and 0.1 mol of potassium carbonate was changed to 0.2 mol. As a result, 7.7 g of dimethylhexahydropyridazine-1,2-dicarboxylate having a boiling point of 95°–100° C./3 mmHg, was obtained. The yield was 76.2%.

EXAMPLE 5

The reaction was conducted in the same manner as in Example 1 except that diethylhydrazine dicarboxylate was changed to dimethylhydrazine dicarboxylate (but, the same molar amount was used). As a result, 8.5 g of dimethylhexahydropyridazine-1,2-dicarboxylate having a boiling point of 95°–100° C./3 mmHg, was obtained. The yield was 84%.

EXAMPLE 6

Into a 100 ml four necked flask equipped with a reflux condenser, a stirrer and a thermometer, 8 g (0.033 mol) of dibenzoylhydrazine, 1 g (0.025 mol) of sodium hydroxide and 60 ml of water were charged and heated to 90° C., and 27 g (0.125 mol) of dibromobutane and 37.5 g (0.31 mol) of 33.3% sodium hydroxide were dropwise added under stirring. The mixture was refluxed under heating for 4 hours to complete the reaction. Post treatment was conducted by a usual method to obtain 8.9 g of dibenzoylpyridazine having a melting point of 125°–128° C. The yield was 92%.

REFERENCE EXAMPLE

Preparation of hexahydropyridazine

Into a 100 ml four necked flask equipped with a reflux condenser, a stirrer an da thermometer, 7.12 g (0.03 mol) of diethylhexahydropyridazine-1,2-dicarboxylate and 30 ml of 36% hydrochloric acid were charged and refluxed under heating and stirring. 24 hours later, 80 ml of ethanol was added thereto, and an aqueous hydrochloric acid solution was azeotropically distilled to remove water, and the obtained crystals were collected by filtration. These crystals were suspended in 30 ml of ethanol, and 3.7 g of potassium hydroxide was gradually added under stirring at room temperature while suppressing the heat generation, and the mixture was refluxed under heating for 2 hours. After the reaction, the precipitated salt was removed by filtration, and the filtrate was distilled under reduced pressure to obtain 2.14 g of hexahydropyridazine having a boiling point of 65° C./100 mmHg. The yield was 83%.

I claim:

1. A process for producing a hexahydropyridazine-1,2-dicarboxy compound represented by the formula:

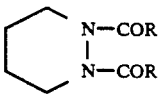 (3)

(wherein R has the same meaning as R in the following formula (1)), which comprises reacting a hydrazine dicarboxy compound represented by the formula:

$$ROC-NH-HN-COR \quad (1)$$

(wherein R is an alkoxy group or an aryl group) with a dihalogenobutane represented by the formula:

$$X-CH_2CH_2CH_2CH_2-X \quad (2)$$

(wherein X is a chlorine or bromine atom) in the presence of a base selected from an alkali metal carbonate or hydroxide, wherein when R is alkoxy, said base is an alkali metal carbonate.

2. The process of claim 1, wherein when R is aryl, said base is an alkali metal hydroxide.

* * * * *

UNITED STATES PATENT AND TRADEMARK OFFICE
CERTIFICATE OF CORRECTION

PATENT NO. : 5,310,738
DATED : May 10, 1994
INVENTOR(S) : Tadashi NAKAYAMA

It is certified that error appears in the above-indentified patent and that said Letters Patent is hereby corrected as shown below:

On the title page, Item [86], the § 371 and § 102(e) Dates should read as follows:

--Aug. 25, 1992--

Signed and Sealed this

Ninth Day of August, 1994

*Attest:*

BRUCE LEHMAN

*Attesting Officer*     *Commissioner of Patents and Trademarks*